United States Patent [19]

Graunke

[11] 4,229,264

[45] Oct. 21, 1980

[54] METHOD FOR MEASURING THE RELATIVE ETCHING OR STRIPPING RATE OF A SOLUTION

[75] Inventor: Donald R. Graunke, Seattle, Wash.

[73] Assignee: The Boeing Company, Seattle, Wash.

[21] Appl. No.: 957,742

[22] Filed: Nov. 6, 1978

[51] Int. Cl.² ............................................. B01D 59/40
[52] U.S. Cl. ...................................................... 204/1 T
[58] Field of Search .......................... 204/1 T, 195 R; 156/626, 627; 73/61 R

[56] References Cited

U.S. PATENT DOCUMENTS

| 1,845,231 | 2/1932 | Browning | 204/144.5 |
|---|---|---|---|
| 2,791,473 | 5/1957 | Mattox | 368/114 |
| 3,375,178 | 3/1968 | Locke | 204/1 T |
| 3,859,193 | 1/1975 | Bednarski et al. | 204/195 H |
| 3,904,487 | 9/1975 | Lieberman et al. | 204/1 T |

OTHER PUBLICATIONS

Marsh et al., "Analytical Chemistry," vol. 38, No. 11, Oct. 1966, pp. 1498–1502.
Seddon, "The Metal Industry," Jan. 15, 1943, pp. 37 & 38.

*Primary Examiner*—G. L. Kaplan
*Attorney, Agent, or Firm*—Christensen, O'Connor, Johnson & Kindness

[57] ABSTRACT

A pair of relatively inert metal electrodes 14 and 16 are immersed in a metal processing solution 10. The metal processing solution 10 is of the type that oxidizes a metal dissimilar from that of the electrodes from the elemental state to the ionic state. A predetermined potential is applied for a predetermined time across the electrodes to create a direct current through the solution, thereby plating a determinable quantity of the metal ionic species on one of the electrodes as a metal. After the potential is removed from the electrodes, the elapsed time required for essentially all of the metal to be reoxidized to the ionic state by the processing solution is measured. Since the plated metal is dissimilar from that of the electrode, a galvanic cell is formed. Thus, the elapsed time can be measured, for example, by coupling an external load in series with the two electrodes and noting the elapsed time during which a current flows through the load. The elapsed time thus measured provides a direct indication of the etching or stripping rate of the solution.

6 Claims, 2 Drawing Figures

METHOD FOR MEASURING THE RELATIVE ETCHING OR STRIPPING RATE OF A SOLUTION

BACKGROUND OF THE INVENTION

The present invention relates to methods for chemical process control, and more particularly to methods for determining the strength of a metal processing solution that is capable of spontaneously oxidizing the metal from its elemental state to its ionic state, and thus for determining the etching or stripping rate of the solution.

Etching and stripping solutions are used widely throughout industry to etch or strip unwanted surface layers from metal parts. For example, copper etching solutions, primarily comprising ammonium persulfate, are utilized to strip unwanted copper from masked, copper plated circuit board substrates to produce printed circuit boards. All such solutions function by oxidizing the unwanted metal from its elemental state to its ionic state. As the metal ions build up in the solution, the etching or stripping capability of the solution is decreased in proportion to the increase in concentration of the metal ion. In the past, difficulties have been encountered in quickly and accurately determining when the metal ion concentration has built up sufficiently to render the oxidation rate of the solution too slow to be economically functional.

Heretofore, analytical chemistry techniques have been employed to determine the concentration of the metal ions in processing solutions. Although these techniques are effective and accurate, they suffer from one or more of the drawbacks of being cumbersome, time consuming, or relatively expensive to perform. The amount of time required to monitor the metal ion concentration can be especially quite important. For example, by the time it is determined that a solution has a high metal concentration using conventional analytical techniques, valuable production time that could have been gained by replacing or replenishing the solution has been lost.

It is therefore an object of the present invention to provide methods for quickly and accurately determining the relative strength of metal processing solutions. More particularly, it is an object of the present invention to provide methods that are especially adapted to determine the etching rates of etching and stripping solutions that chemically function to oxidize a metal from its elemental state to its ionic state. Further objects of the present invention are to provide such methods that are simple and economical to perform, that involve little time to complete, that are accurate and reproducible, that can be performed on a production solution at the production site, and that require no particular expertize to provide accurate, reproducible, and easily interpretable results.

SUMMARY OF THE INVENTION

Accordingly, the present invention provides methods for determining the relative etching rate of a solution capable of spontaneously oxidizing a metal from its elemental state to its ionic state that fulfill the foregoing objects, and other objects that will become apparent to one of ordinary skill. In its broad aspects, the method requires the application of a predetermined potential for a predetermined time across first and second spaced electrodes composed of a relatively inert metal that are immersed in the processing solution. The current flowing through the solution between the electrodes plates a determinable quantity of the metal ionic species in the solution as a metal on one of the electrodes. Thereafter, the solution is allowed to oxidize the metal previously plated on the electrode back to the ionic species. The elapsed time required for essentially all of the metal on the one electrode to be oxidized to the ionic species is indicative of the relative etching or stripping rate of the solution.

BRIEF DESCRIPTION OF THE DRAWINGS

A better understanding of the present invention can be derived by reading the ensuing specification in conjunction with the accompanying drawings, wherein.

DETAILED DESCRIPTION OF THE INVENTION

The present invention is useful in determining the concentration of a metal or its ionic species in a metal etching or stripping solution or other metal processing solution capable of spontaneously oxidizing the metal from its elemental state to its ionic state, and thus is useful in determining the etching or stripping rate or capability of such solutions. Examples of such solutions include ammonium persulfate copper etching solution, stripping solutions for the removal of metal coatings on a dissimilar metal, stripping solutions for conversion coating removal, and the like. For example, the present invention can be employed to determine the concentration of copper in an ammonium persulate solutions. Additionally, the present invention can be employed to determine the cadmium, cadmium/tin, zinc, silver, copper, tin, or gold concentration in steel stripping solutions composed of aqueous sodium hydroxide and sodium cyanide; the chromium concentration in sodium hydroxide/sodium carbonate steel stripping solution; and the manganese content in an aqueous chromic acid stripping solution for removing a manganese phosphate conversion coating from a ferrous base metal. The foregoing examples are only a few of the many kinds of metal processing solution combinations in which the metal concentration and the etching rate can be determined in accordance with the present invention.

Figure 1:
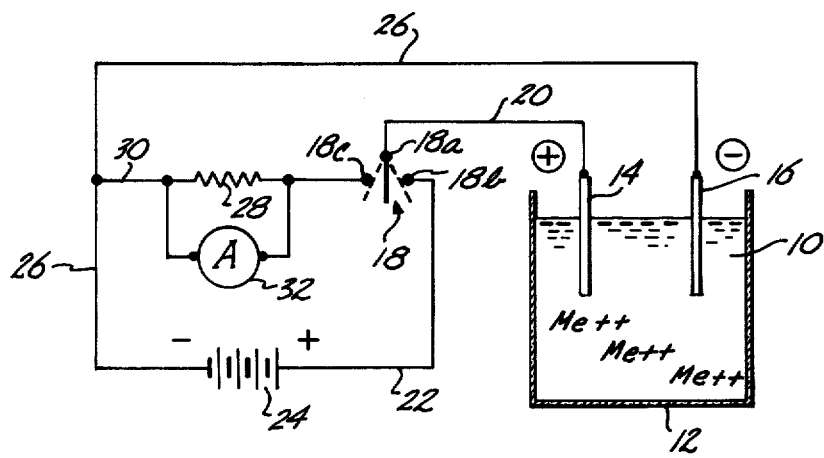
FIG. 1 is a schematic diagram of a simple circuit that can be used to perform the preferred method of the present invention.

The concentration of a metal or its ionic species can be determined in accordance with the present invention by utilizing an apparatus embodying the circuit illustrated in FIG. 1. Referring to FIG. 1, a metal processing solution 10 such as an aqueous ammonium persulfate solution normally employed to etch copper from a substrate is placed in a container 12. The container 12 can be the commercial processing container in which the parts from which copper is to be etched are normally placed in commercial production. Two electrodes 14 and 16 are immersed in the solution 10. The electrodes are composed of a metal that is relatively inert when placed in the solution and that is dissimilar from the metal ion in the solution on which the concentration determination is to be made. For all of the solutions specifically discussed in the foregoing paragraph, platinum electrodes are preferred. The material of which the electrodes are composed must necessarily be inert relative to the oxidizing capability of the metal processing solution. That is, the electrodes cannot be subject to rapid oxidative attack by the solution. One of the electrodes 14 is coupled to the common terminal 18a of a single pole, double throw switch 18 via lead 20. One remote terminal 18b of the switch 18 is coupled via lead 22 to the positive terminal of a battery 24. The negative terminal of the battery 24 is coupled via lead 26 to the other electrode 16. A resistor 28 is coupled in series by leads 26 and 30 between the other electrode 16 and the other remote terminal 18c of the switch 18. An ammeter 32 has its terminals coupled in parallel with the resistor 28. Thus, when the switch elements of switch 18 couples the common terminal 18a with the first remote terminal 18b, the electrodes 14 and 16 are coupled in series with the battery 24, rendering the electrode 14 anodic and the electrode 16 cathodic. When the switch element of switch 18 electrically couples the common terminal 18a and the other remote terminal 18c, the load represented by the resistor 28 and the ammeter 32 is coupled in series with the electrodes 14 and 16.

In use in accordance with the present invention, the electrodes 14 and 16 are first immersed in the oxidizing solution containing a metal ion, the concentration of which is to be determined. The switch element of switch 18 is moved to electrically couple the common terminal 18a to the remote terminal 18b, thus placing the battery 24 in series with the two electrodes 14 and 16. Immediately, a direct current flows between the electrodes 14 and 16 in the solution. Metal ions present in the solution 10 immediately begin to plate onto the cathode 16. The battery 24 is maintained in series connection with the electrodes for a predetermined amount of time, for example, on the order of about 30 seconds. Upon expiration of the predetermined plating period, the switch element of switch 18 is disconnected from remote terminal 18b, removing the battery from the circuit, and is immediately connected to remote terminal 18c, thus placing the load represented by resistor 28 and ammeter 32 in series with the two electrodes. A current will flow through the circuit thus formed since a galvanic cell has been formed by the platinum electrode 14 and the dissimilar metal plating on the other electrode 16. At the same time that the switch 18 couples the load into series with the electrodes 14 and 16, a stopwatch is manually started. Alternatively, a timer can be coupled into the circuit and energized upon closing of the switch element across contacts 18a and 18c. The ammeter 32 will indicate that a current is flowing through the circuit coupled to the electrode when the switch 18 couples the ammeter in the circuit. Since the solution 10 is an etching solution, the solution will immediately begin to oxidize the metal ions previously plated onto the electrode 16, thus converting them from their elemental state back to the ionic state in solution. When all of the metal plated onto the electrode 16 has been oxidized by the etching solution, leaving only identical electrodes in contact with the solution and thus destroying the galvanic cell, no current will flow through the load, and thus the ammeter will register zero. When the current indication on the ammeter 32 drops to or substantially to zero, the stopwatch that was started when the ammeter was coupled into the circuit is stopped. The elapsed time indicated by the stopwatch is representative of the relative concentration of the metal ion in the solution 10 and the etching rate of the solution 10.

From the foregoing explanation, one of ordinary skill will readily realize that the amount of metal plated onto the cathodic electrode 16 when the battery 24 is coupled in series with the electrodes is primarily dependent upon the battery potential, upon the amount of time the battery is coupled in series with the electrodes, the temperature of the solution, the concentration of metal ions in the solution, and the activity or strength of the solution itself. Thus, the amount of metal plated onto the electrode in repeated plating cycles with the same solution can be made dependent upon the metal ion concentration in the solution by maintaining the time, temperature and battery potential constant during repeated plating cycles. Moreover, the rate at which metal is etched from the plated electrode is primarily dependent upon the metal ion concentration in the solution, the strength of the solution itself, and the temperature of the solution. Thus the rate at which the given amount of plated metal on an electrode is etched from that electrode by the solution during repeated etching cycles can also be made solely dependent upon the metal ion concentration in the solution by maintaining the concentration of the etchant in the solution and the temperature of the solution at substantially constant levels.

In practice, it is relatively easy to control the variables that one desires to maintain constant for purposes of determining the metal concentration in accordance with the present invention. For example, the temperature of a commercial etching solution is normally mantained at or near room temperature, which does not vary substantially under normal processing conditions. Thus, be always using a constant potential battery and by conducting the plating cycle for a predetermined amount of time, the amount of metal plated onto the cathode and the elapsed time necessary to etch the thus-plated metal from the cathode is representative of and proportional to the etching rate of the solution.

Accordingly, one of ordinary skill will readily recognize that the elapsed time required for the solution to etch the plated metal from the cathode can also be directly correlated to the concentration of the metal ion in the process solution. By following the foregoing procedure on solutions of known concentration and recording the elapsed time required to completely etch the plated metal from the cathode for each solution of varying concentration, and correlating the elasped time with the known concentration levels in tabular or graphic form, one has a handy process control tool with which the actual concentration of a commercial processing solution can be determined in a relatively short time, normally on the order of less than one minute. Once the elapsed time versus known concentration information has been recorded, simply by following the same procedure employed to record the known information on a solution of unknown concentration, recording the elapsed time, and comparing that elapsed time with the tabular or graphic information, the actual metal ion concentration of the solution, and thus the stripping or etching rate of the solution, can readily be deduced.

EXAMPLE

The present invention can be better understood by reference to the following specific Example. This Example is not intended to delimit the broad concepts disclosed herein, but is intended to more specifically teach one of ordinary skill how to make and use the subject invention.

A fresh, aqueous, ammonium persulfate solution containing 240 g/l of ammonium persulfate was placed in a commercial etching tank. The temperature of the solution was maintained constant at about 23° C. Copper parts to be etched were placed in the tank in the ordinary course of production of printed circuit boards. Periodically, aliquots of the commercial ammonium persulfate solution were removed from the tank and analyzed for copper content by conventional analytical chemistry procedures. At the same time that the aliquots were removed from the commercial etching solution, elapsed etching time measurements were made in accordance with the present invention. An apparatus embodying the circuit as shown in FIG. 1 was used to make the elapsed time determinations. The electrodes 14 and 16 were composed of platinum, the battery 24 had a potential of 6 volts. The ammeter 32 had an internal resistance of about 95.5 ohms, and the resistor 28 had a value of 1000 ohms. The battery 24 was coupled into series with the electrodes for exactly 30 seconds for the plating portion of each test cycle. Immediately after the 30 second plating period, the battery was removed from the circuit and the load comprising the ammeter 32 and the resistor 28 was coupled into series with the electrode by manipulation of the switch 18. Immediately upon coupling the load into series with the electrodes, a stopwatch was started. As soon as the current reading on the ammeter dropped to zero, the stopwatch was stopped and the elapsed time for the etching portion of each test cycle was recorded.

Figure 2:
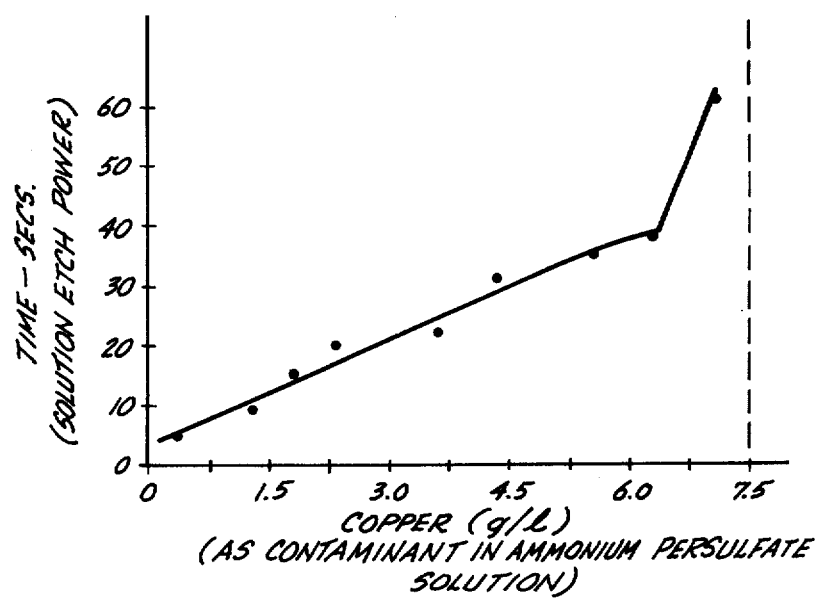
FIG. 2 is a graph of copper concentration in grams per liter in an ammonium persulfate copper etching solution versus the elapsed time required for the solution to completely oxidize a determinable amount of metal plated onto one of the electrodes illustrated in FIG. 1 in accordance with the present invention.

The elapsed time for each test cycle and the analytically determined copper content of the aliquot extracted from the solution at the time each test cycle was conducted were correlated and plotted on the graph of FIG. 2. As can be observed from FIG. 2, as the copper content in the ammonium persulfate solution increased, the elapsed time reading taken in accordance with the present invention also increased. As the copper content approached the specification limit, that is, the copper concentration at which the etching rate of the solution becomes economically unattractive, it can be observed that the elapsed time reading taken in accordance with the present invention increased more rapidly than for lower copper contents.

As explained above, since the increasing elapsed etching time is directly correlatable to the copper content of the etching solution, the copper concentration in an ammonium persulfate solution of unknown concentration at the same temperature and same ammonium persulfate concentration as that used for the foregoing Example can be determined by merely running the elapsed etching time determination in accordance with the present invention. For example, for an elapsed etching time of approximately 30 seconds, obtained from a used ammonium persulfate copper etching solution in accordance with the procedure just described, the copper concentration of such an ammonium persulfate solution would be about 4.5 g/l as read from FIG. 2.

Although the present invention has been specifically described in conjunction with copper content determinations on an ammonium persulfate etching solution, one of ordinary skill in the art will readily recognize that graphs similar to FIG. 2 can be prepared for any of the other broad range of solutions described in the foregoing specifications. Thus the present invention has wide applicability to general use with metal oxidizing solutions. After reading the foregoing specification, one of ordinary skill will be able to effect changes, substitutions of equivalents and other alterations without departing from the broad concepts disclosed herein. Accordingly, it is intended that the protection afforded by Letters Patent hereon be limited only by the definitions contained in the appended claims and equivalents thereof.

The embodiments of the invention in which an exclusive property or privilege is claimed are defined as follows:

1. A method for providing an indication of the relative etching rate of a partially depleted oxidizing metal processing solution, said solution being partially depleted as a result of spontaneously oxidizing a metal to a dissolved metal ionic species, comprising the steps of:
   (a) immersing in said solution first and second spaced electrodes each composed of a metal relatively inert with respect to said solution;
   (b) applying a predetermined potential for a predetermined time across said electrodes to create a direct current through said solution between said electrodes to plate a determinable quantity of said metal ionic species as a metal plating on one of said electrodes;
   (c) thereafter allowing said solution to oxidize said metal plating back to said ionic species without applying a potential to said electrodes; and
   (d) measuring the elapsed time required for substantially all of said metal plating on said one electrode to be oxidized back to said ionic species.

2. The method of claim 1 wherein said solution is a metal etching solution.

3. The method of claim 1 wherein said solution is a metal stripping solution.

4. The method of claim 1 wherein said electrodes are platinum.

5. The method of claim 1 wherein steps (b) and (c) are conducted at substantially the same temperature.

6. The method of claim 1 wherein said elapsed time is measured by coupling an electrical load external to said solution across said electrodes at the end of said predetermined time, monitoring the current flow through said load, and measuring the elapsed time from the point when the load is coupled to said electrodes to the point at which current substantially ceases to flow through said load.

* * * * *